US00PP36886P2

(12) United States Plant Patent
Hansen

(10) Patent No.: US PP36,886 P2
(45) Date of Patent: Aug. 12, 2025

(54) ***PHLOX* PLANT NAMED 'Dream Girl'**

(50) Latin Name: *Phlox paniculata*
Varietal Denomination: Dream Girl

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,466

(22) Filed: Jan. 29, 2025

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02
See application file for complete search history.

*Primary Examiner* — Kent L Bell

(57) ABSTRACT

A new and unique hybrid cultivar of *Phlox* plant named *Phlox* 'Dream Girl' of tall, sturdy, multi-stemmed, upright habit. Dark-green foliage is thick with exceptional powdery mildew resistance on stiff stems. Lavender-pink flowers with strong white eyes are produced on large heads of branched peduncles and nearly cover the top of the plant beginning mid-July and continuing and reblooming for about seven weeks through late summer. 'Dream Girl' is especially suitable as a potted plant, for the garden, for attracting hummingbirds and butterflies, and for cut flower arrangements.

1 Drawing Sheet

Botanical classification: *Phlox paniculata.*
Variety denomination: 'Dream Girl'.

STATEMENT REGARDING PRIOR DISCLOSURES UNDER 37 CFR 1.77(B)(6)

The first offer for sale in the form of a website with a photograph and brief description was on Feb. 1, 2024, maintained by Walters Gardens, Inc. Subsequently, Walters Gardens, Inc. published an advertisement in their "Walters Gardens 24-25 Catalog" on May 23, 2024. Walters Gardens, Inc. obtained the new plant and all information relating thereto, from the inventor. No plants of *Phlox* 'Dream Girl' have been sold, in this country or anywhere in the world, under this or any name, nor has any disclosure of the new plant been made more than one year prior the filing date of this application, and such sale or disclosure within one year was either derived directly or indirectly from the inventor.

BACKGROUND OF THE INVENTION

The present invention relates to a new and distinct Tall *Phlox* cultivar of *Phlox* plant, known as *Phlox* 'Dream Girl' and will be referred to hereafter by its cultivar name or the "new plant". The new plant was the result of a controlled pollination of 'Cover Girl' U.S. Plant Pat. No. 32,323 as the female or seed parent and the proprietary, unreleased hybrid known as 14-592-5 (not patented) as the male or pollen parent. The cross was performed by the inventor on Jul. 6, 2017, in the trial gardens at a wholesale perennial nursery in Zeeland, Michigan, and seed was collected in the autumn of 2017. During the trial process the new plant arising as a single seedling selection from the identified cross was identified by the breeder code 17-36-6. 'Dream Girl' has been asexually propagated by division at the same nursery in Zeeland, Michigan since 2019, as well as by shoot tip tissue culture starting in 2020. The unique characteristics of the new plant have been found to be reproducible and stable in successive generations of asexually propagated plants and the resultant plants have been found to be identical to the original selection.

BRIEF SUMMARY OF THE PLANT

*Phlox* 'Dream Girl' is unique from its parents and all other tall garden *Phlox* or other hybrid *Phlox* known to the inventor. The closest comparison cultivars known to the inventor are: 'Prismatic Pink' U.S. Plant Pat. No. 35,787, 'Balsukapin' U.S. Plant Pat. No. 33,188, 'Balsukalav' U.S. Plant Pat. No. 33,022, 'Balkapopur' U.S. Plant Patent No. 30,781, 'Glamour Girl' U.S. Plant Pat. No. 25,778, 'Material Girl' U.S. Plant Pat. No. 36,444.

'Prismatic Pink' has a bubblegum pink flower with dark pink eye. 'Balsukapin' has a much shorter habit and the flowers do not have a strong white eye. 'Balsukalav' is shorter in habit and has a slightly more reddish hue of the flower face without the white eye. 'Balkapopur' has a smaller habit and slightly darker flower without the white eye. 'Glamour Girl' is slightly taller and has flowers that are more hot coral pink without a white eye. 'Material Girl' has a slightly larger habit and fuchsia-purple flowers with darker eyes, and the stems have darker brown striations.

The female parent is much taller in habit with lavender purple flowers and a white eye halo. The male parent has a more compact habit, magenta flowers with a white eye and darker wine-colored stems.

'Dream Girl' differs from all other *Phlox* known to the inventor in the following repeatedly observed traits in combination:

1. Tall plants of sturdy upright habit producing clean, dark-green, lanceolate leaves;
2. Showing exceptional powdery mildew resistance;

3. Multiple stems produce large branched mounds of flowers starting in mid- July for about seven weeks;
4. Flowers on strong stiff stems producing lavender-pink flowers with a strong white eye;
5. Flowers cover nearly the entire top of the plant;

BRIEF DESCRIPTION OF THE DRAWINGS

The photographs of the new plant demonstrate the unique traits of 'Dream Girl' and the overall appearance of three-year-old plants grown in a full sun trial garden in Zeeland, Michigan. The colors are as accurate as reasonably possible with color reproductions. Variation in ambient light spectrum, source and direction may cause the appearance of minor variation in color.

DETAILED BOTANICAL DESCRIPTION

Figure 1:
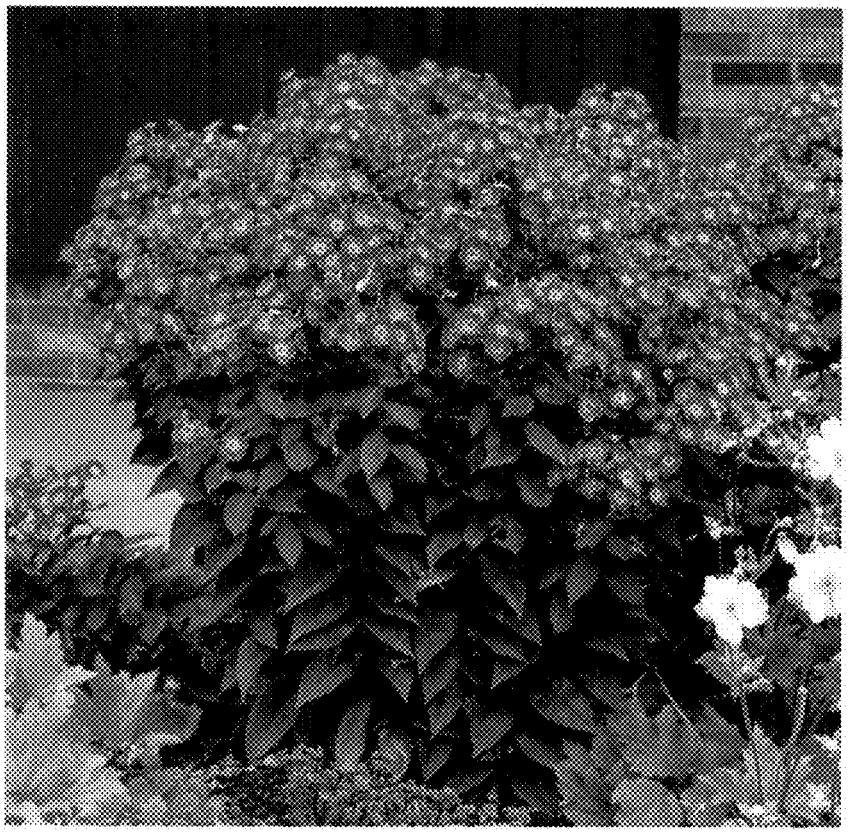
FIG. 1 shows the habit of the new plant just beginning to flower in the landscape.
Figure 2:
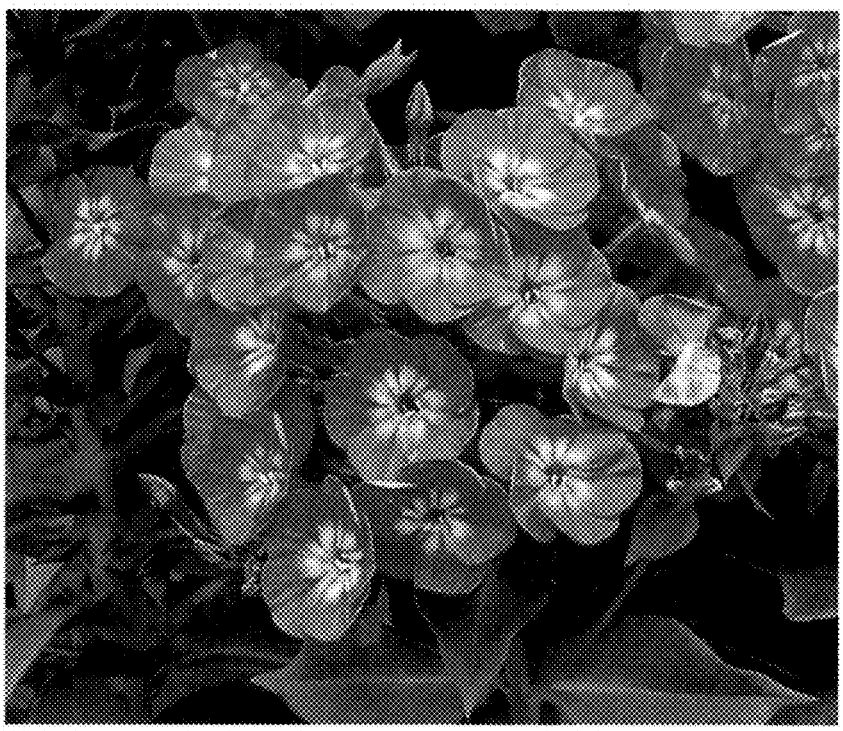
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Dream Girl' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full sun garden of a wholesale perennial nursery in Zeeland, Michigan with supplemental fertilizer and water as needed.

Botanical classification: *Phlox paniculata;*

Parentage: 'Cover Girl' as the female or seed parent and 14-592-5 as the male or pollen parent;

Plant habit: Hardy herbaceous perennial, densely upright, producing about 28 rigid mostly upright stems; flowering at up to 90 cm tall and about 79 cm wide; flowering begins mid-July in Michigan and continuing for about 7 weeks with repeating into late summer;

Propagation: Stem cuttings; rooting in about 21 days;

Time to produce finished crop in 3.8-liter pots: About 10 to 12 weeks from a 25 mm liner; moderate rate of growth;

Root: Primary roots to about 1.0 mm thick; secondary fibrous and freely branching; color creamy white to tan depending on soil type; color of active roots nearest RHS NN155B depending on soil components;

Leaves: Simple; opposite; lanceolate; narrowly acute apex; attenuate base; sessile; entire margin; tough, coriaceous;

Leaf size: To about 13.5 cm long by about 57 mm wide; average about 12.5 cm long by about 30 mm wide; becoming smaller distally;

Leaf surfaces: Glabrous and lustrous adaxial, glabrous and matte abaxial;

Leaf color expanding: Variable; adaxial between RHS 145A and RHS 146D, nearest RHS 137B, with moderate blush of nearest RHS 187A; abaxial nearest RHS 147B with moderate blush of nearest RHS 187A;

Leaf color at flowering: Adaxial nearest RHS 137A, abaxial between RHS 147B and RHS 147C;

Foliage fragrance: None detected;

Veins: Pinnate; glabrous adaxial and abaxial; midrib about 1.5 mm wide at base, slightly sunken adaxial and raised abaxial;

Vein color: Adaxial midrib, primary, and secondary veins nearest RHS 146D; abaxial midrib and primary veins between RHS 137A;

Petiole: Leaves sessile;

Stems: About 15 per plant; cylindrical; stiff; wiry; strong; mostly upright; glabrous; to about 42 cm long and 9 mm diameter at base, average about 38 cm long and 7 mm diameter at base;

Stem color: Nearest RHS 146D with variable blush to nearly solid RHS 187A strongest in portions of highest sun exposure;

Nodes: About 18 per stem below initial flowers plus 17 nodes in branched flower head; average internode length about 2.7 cm;

Node color: Nearest RHS 146D;

Inflorescence: A loosely-branched compound corymb of about 120 flowers; flowering portion average about 30 to 45 cm long and 38 cm wide;

Flowers: Perfect; salverform with flat face and long fused tube; actinomophic; typically with five petals; about 29 mm long total with tube about 27 mm long and 2.5 mm diameter at base and 5 mm diameter below face; face about 34 mm across; glabrous adaxial and abaxial face, adaxial corolla tube glabrous except densely puberulent from 4 to 8 mm from base, abaxial corolla tube lightly puberulent; aspect upright to slightly outward; self-cleaning;

Flower longevity: Individually about 5 days on plant or as cut flower;

Flower fragrance: Lightly sweet;

Buds one to two days prior to opening: Clavate; acute apex with petals convolute and implicate about each other; base fused; total bud about 26 mm long, tube about 15 mm long and 3 mm diameter in tube, bulb about 11 mm long and swollen to 6 mm diameter toward apex; calyx adpressed to corolla tube;

Bud color: Bulb portion petal margins nearest RHS N82A with petal centers nearest RHS N81B, exposed corolla tube nearest RHS N79C, and calyx margins variable between RHS NN155B to RHS 72B, center distally nearest RHS 146B and proximally between RHS 146D and RHS 145A with faint to heavy maculate with nearest RHS 187A;

Petals: Five; sympetalous; margin entire; apex rounded; base fused into tube; abaxial and adaxial limb glabrous, abaxial tube surface puberulent, adaxial corolla pubescent between 4 mm and 8 mm from base; limbs strongly imbricate, about 30 percent over the next petal;

Petal size: Limb to about 15 mm wide and about 14 mm long, corolla tube to about 27 mm long and 3 mm diameter at base and 5 mm diameter at the face;

Petal color: (Young) adaxial limb base between RHS 75B and RHS 75C, distal eye from 4 to 8 mm from base nearest RHS NN155D, distal portion and midrib marks through center eye between RHS N78B and RHS NN78C; abaxial limb margin nearest RHS N82D thinly striated with between RHS N81C and RHS N81D, abaxial corolla tube between RHS N82C and RHS N82D with stripes of nearest RHS N82A; adaxial corolla tube basal 2 mm nearest RHS NN155D, distally nearest RHS NN78D;

Petal color: (Mature) adaxial limb base nearest RHS N74C with eye between RHS N74C and RHS NN155B, distally nearest N78A; corolla tube nearest RHS N78D in distal portion, basal 2 mm nearest RHS NN155D; abaxial limb outer portion nearest RHS N78A and center portion nearest RHS N82D thinly striated with between RHS N81C and RHS N81D, abaxial corolla tube between RHS N82C and RHS N82D with stripes of nearest RHS N82A;

Androecium: Five;

*Filaments*.—Typically five; straight; cylindrical; adnate to adaxial corolla tube except free in distal 1 mm; varying lengths between 25 mm and 18 mm, about 0.2 mm in diameter; color nearest RHS NN155C in the distal 1 to 3 mm and proximally between RHS 85C and 84D.

*Anther*.—Five; oblong elliptic; dorsifixed; longitudinal; about 4 mm long by 1 mm wide; color nearest RHS 10C.

*Pollen*.—Abundant; color nearest RHS 18B.

Gynoecium: One pistil per flower; to about 25 mm long;

*Style*.—Cylindrical; straight; about 22 mm long and about 0.3 mm diameter; persistent after flower abscission; color proximal half nearest RHS 145C and distal half nearest RHS N77D.

*Stigma*.—Trifid in the distal 1 mm, about 0.3 mm in diameter; color nearest RHS 2D.

*Ovary*.—Superior; conical; acute apex, base truncate; about 2 mm long and 1 mm diameter; color nearest RHS 144A.

Calyx: Tubular; adpressed to corolla tube; to about 10 mm long, 4 mm cross at apex, and 3 mm diameter at base;

Sepals: Five; linear; narrowly acute apex, margin entire; basal 5 mm fused; abaxial surface matte and adaxial slightly lustrous; persistent; individually about 10 mm long and 1.5 mm wide;

Sepal color: Adaxial nearest RHS 146B with fine spotting of nearest RHS 187A, margin translucent to nearest RHS N77D; abaxial margins variable between RHS NN155B to RHS 72B, center distally nearest RHS 146B and proximally between RHS 146D and RHS 145A with faint to heavy maculate with nearest RHS 187A;

Peduncle: Glabrous, stiff, strong, moderately lustrous, upright, cylindrical; flowering portion about 30 to 45 cm long and 38 cm wide; and 4 mm diameter below flower branches; about 16 to 18 branches to about 16 cm long and 2.5 mm diameter at base;

Peduncle color: Nearest blend of RHS 146D and RHS 145A with moderate blush of nearest RHS 187C in regions of high light intensity;

Bracts: Lanceolate; ciliolate margin; acute apex; sessile truncate base; glabrous; subtending upper branches and flowers; to about 40 mm long and 10 mm across;

Bract color: Adaxial nearest RHS 137A, abaxial between RHS 147B and RHS 147C;

Pedicel: Cylindrical; glabrous; to about 4 mm long and 1 mm diameter; aspect upwardly to slightly outwardly;

Pedicel color: Nearest RHS 146D maculate with nearest RHS 187A;

Fruit and seeds have not yet been observed.

Hardiness and culture: The new plant grows best with plenty of moisture and adequate drainage; hardy to at least from USDA zone 4 through 8.

Disease resistance: *Phlox* 'Dream Girl' demonstrated excellent powdery mildew resistance caused by *Erysiphe cichoracearum* in the presence and under conditions of intense pressure that would normally show symptoms.

I claim:

1. A new and distinct cultivar of hybrid *Phlox* plant named *Phlox* 'Dream Girl', as herein described and illustrated.

* * * * *